United States Patent [19]

Pohl

[11] Patent Number: 4,659,756

[45] Date of Patent: Apr. 21, 1987

[54] FATTY ETHENOID ACYLAMINOORGANOSILICON COMPOUNDS AND THEIR USE IN COMPOSITIONS FOR COATING GLASS

[75] Inventor: Eric R. Pohl, Thornwood, N.Y.

[73] Assignee: Union Carbide Corporation, Danbury, Conn.

[21] Appl. No.: 761,893

[22] Filed: Aug. 2, 1985

Related U.S. Application Data

[62] Division of Ser. No. 563,980, Dec. 20, 1983, Pat. No. 4,548,842.

[51] Int. Cl.⁴ ............... C08L 63/00; C08L 83/00; C08L 72/01
[52] U.S. Cl. .................... 523/402; 524/579; 524/582; 524/585; 524/612; 525/106; 525/409; 525/530
[58] Field of Search .............. 525/106, 409, 530; 523/402; 524/579, 582, 585, 612

[56] References Cited

U.S. PATENT DOCUMENTS

| | | | |
|---|---|---|---|
| 2,928,858 | 3/1960 | Morehouse | 260/448.8 |
| 2,929,829 | 3/1960 | Morehouse | 260/448.2 |
| 2,995,533 | 8/1961 | Parmer et al. | 260/23 |
| 3,249,461 | 5/1966 | TeGrotenhuis | 117/76 |
| 3,537,882 | 11/1970 | Wiggill | 117/72 |
| 3,681,266 | 8/1972 | Domba | 260/25 |
| 3,720,699 | 3/1973 | Stoddard | 260/448.8 |
| 3,746,738 | 7/1973 | Pepe et al. | 260/46.5 |
| 3,755,354 | 8/1973 | Holub et al. | 260/326 |
| 3,787,439 | 1/1974 | Holub et al. | 260/326 |
| 3,801,361 | 4/1974 | Kitaj | 117/124 |
| 3,959,327 | 5/1976 | Pepe et al. | 260/448.8 |
| 3,998,985 | 12/1976 | Kitaj | 427/386 |
| 4,130,677 | 12/1978 | Huntsberger | 427/379 |
| 4,209,455 | 6/1980 | Pepe . | |
| 4,224,365 | 9/1980 | Ali-Zaidi | 427/421 |
| 4,250,068 | 2/1981 | Ali-Zaidi | 260/28.5 |
| 4,284,548 | 9/1981 | Kaufman et al. | 260/38 |

FOREIGN PATENT DOCUMENTS 0057595 8/1982 European Pat. Off. .

*Primary Examiner*—Lewis T. Jacobs
*Attorney, Agent, or Firm*—P. W. Levzzi; B. W. Stegman

[57] ABSTRACT

Fatty ethenoid acylaminoorganosilicon compounds have been found to enhance the surface properties of glass articles. The fatty ethenoid acylaminoorganosilicon compound can be applied as a coating to the glass article's surface either alone or in combination with dispersing agents and organic polymers and/or fatty acids.

7 Claims, No Drawings

FATTY ETHENOID ACYLAMINOORGANOSILICON COMPOUNDS AND THEIR USE IN COMPOSITIONS FOR COATING GLASS

This application is a division of prior U.S. application Ser. No. 563,980, filed 12/20/83, now U.S. Pat. No. 4,548,842, issued 10/22/85.

BACKGROUND OF THE INVENTION

1. Field of the Invention

The instant invention relates to a class of acylaminoorganosilicon compounds and their use in compositions for coating glass and especially glass containers. More specifically, the class of acylaminoorganosilicon compounds are those containing a fatty ethenoid substituent.

2. Prior Art

Acylaminoorganosilicon compounds have been generally known since the pioneering work performed by Morehouse as reported in U.S. Pat. Nos. 2,929,829 and 2,928,858. The novel acylaminoorganosilicon compounds taught in these references were considered useful as, among other things, acid-base indicators; additives for silicon products, such as oils and gums; thermosetting resins for coating materials; and ultraviolet ray absorbers.

Subsequent to the work performed by Morehouse, improvements based on new and useful acylaminoorganosilicon compounds were discovered. In U.S. Pat. No. 3,249,461, the use of a conjugated olefin containing acylaminoorganosilicon compounds was taught as effective fiber glass reinforcing agents. In U.S. Pat. No. 3,681,266, a distinct class of acylaminoorganosilicon compounds was fluorine modified to provide a coating material that is useful as a water repellant. In U.S. Pat. No. 3,720,699, a new and useful class of haloorganoacylaminoorganosilicon compounds are reported to be useful as a coating material.

A variance on the theme, U.S. Pat. No. 3,755,354 is directed to amide acid and imido-substituted organosilicon compounds that are reportedly useful as glass fiber coupling agents. In a closely related U.S. Pat. No. 3,787,439, imido-substituted organopolysiloxanes were disclosed, including conjugated, unsaturated acylaminoorganosilicon compounds, as additives for glass fibers.

In U.S. Pat. No. 3,959,327, acylaminoorganosilicon compounds with thio-containing substituents were reported as plasticizers and coupling agents.

A new class of complex acylaminoorganosilicon compounds was reported in U.S. Pat. Nos. 4,209,455 and 4,284,548. In each the mono- and bis-silanes were characterized by a single acylamino group and at least one secondary or tertiary aminoorgano group. These novel compositions were considered useful in fiber sizes.

In U.S. Pat. No. 3,746,738, acylaminoorganosilicon compounds that contained various pendant silanes were described as useful glass fiber sizes.

In U.S. Pat. No. 3,537,882, silylated polymers were prepared by amidation of acid chloride modified polymers with aminoorganosilanes for use as coating materials.

CA 84:59633W teaches stearoyl and oleoyl acylaminoorganosilicon compounds.

In U.S. patent application Ser. No. 537,671 filed Sept. 30, 1983, now U.S. Pat. No. 4,584,138, acylaminoorganosilicon compounds containing fatty ethenoid groups are described as useful glass fiber sizes.

It is well known in the art that glass derives its strength from an unblemished surface and any scratches or flaws which are present on the surface decreases the strength of the glass many-fold. Glass articles, such as bottles, sheets and fibers possess their maximum strength shortly after they are formed. Their strength rapidly diminishes when they are subjected to abrasive contact in the course of handling, packaging and shipping.

This problem is illustrated for glass containers that are use by processors of food and beverages. The glass containers are subjected to a number of processing operations. The containers are washed, filled, closed, labelled and packaged for delivery. During these operations, the glass containers are rubbed or otherwise contacted in various ways, often under high pressure, which can cause scratching. The glass containers repeatedly come into contact with each other as they move from station to station and during the various washing, filling, closing and packaging operations. Although the need for a glass protective coating was described for glass containers, these are other applications in which this coating for glass articles will be useful.

Numerous references to compositions and materials used as protective coatings exist in the patent literature for glass surfaces. The most widely used protective coatings, for glass bottles, include tin and titanium compounds such as titanium and stannic halides and alkyl titanates. These materials are sprayed on the surface of the glass at a temperature of from 480° C. to 640° C. The tin and titanium compounds are believed to react with moisture in the air to form a $TiO_2$ or $SnO_2$ layer. After the glass is annealed to about 230° C. or lower, a second coating that consists of a polyethylene emulsion, is applied as described in U.S. Pat. Nos. 2,995,533, 3,598,632, 3,496,825, 3,853,612 and 4,272,587. The coating system described in these patents provide a very good protective finish to the glass surface. The coating, however, is very expensive. The price of the intermediates, such as the stannic halide or titanium compounds, the two step application, and the damage to the metal equipment resulting from the corrosive nature of the metal halides all contribute to the unit cost of this coating.

Protective aqueous coating compositions consisting of an organofunctional silane and an organic polymer, such as, for example, vinyl polymers (U.S. Pat. No. 3,998,985), polyamino-acrylate esters (U.S. Pat. Nos. 4,224,365 and 4,250,068) and epoxy (U.S. Pat. No. 4,056,208, and European Patent application No. 82300480.9) are either difficult to apply, i.e. require a primer coat, costly or do not possess the combination of properties required for the glass application, such as for bottles.

Attempts to circumvent the above problems consisted of coating the glass surfaces with an aqueous emulsion of an olefin such as polyethylene and a silane, such as polyethyleneaminepropyltrimethoxysilane or an ethylenediaminopropyltrialkoxysilanes, (U.S. Pat. No. 3,873,353) or a alkyltrialkoxysilane, (U.S. Pat. No. 3,801,361) or gamma-aminopropyltriethoxysilane, (U.S. Pat. No. 4,130,677) or simply an aqueous solution of a silane and an amine salt of acetic acid, (U.S. Pat. No. 3,438,801). While good abrasion resistance and "labelability" are alleged for these coatings, the adhesion of the coating to the bottle when subjected to an aqueous wash, especially aqueous caustic wash, is too low for certain applications.

Although the art is replete with improvements in and modifications of compositions containing organofunctional silanes that are used to coat glass, it is believed that the instant fatty ethenoid acylaminoorganosilicon compounds containing unsaturation in the fatty constituents are novel as a coating and/or component in a coating for glass articles.

OBJECTIVE OF THE INVENTION

It is an object of this invention to provide a class of acylaminoorganosilicon compounds, in combination with an aqueous emulsion of organic polymer or fatty acid that is useful as a coating for glass articles.

It is a further object of this invention that the class of acylaminoorganosilicon compounds can also be used alone, or dissolved in an organic solvent and/or water as a coating for glass articles.

As a coating for glass surfaces, or as a component of a coating for glass surfaces, it is an object of this invention that the class of acylaminoorganosilicon compounds, whether used alone, or in combination with an aqueous emulsion of organic polymer, or with an organic solvent and/or water yield improved balance between the various glass surface properties, including labelability, appearance, abrasion resistance (wet/dry scratch), lubricity and durability to caustic wash over existing coatings that contain an organofunctional silane.

It is further an object of this invention that as a coating or as a component of a coating for glass surfaces, the class of acylaminoorganosilicon compounds, whether used alone, or in combination with an aqueous emulsion of organic polymer or fatty acid, or in combination with an organic solvent and/or water, are easy to apply to the glass surfaces, and do not generate toxic, corrosive or obnoxious fumes.

Other objects of this invention will become apparent from the detailed disclosure and examples set forth herein.

SUMMARY OF THE INVENTION

In accordance with the present invention, there is provided a coating for glass articles comprising a class of fatty ethenoid acylaminoorganosilicon compounds, that can be used alone or in combination with an aqueous emulsion of an organic polymer or fatty acids or in combination with an organic solvent and/or water. This class of acylaminoorganosilicon compounds containing a fatty ethenoid substituent and is represented by the general formula:

$$Y[N(Y)_cR_{2-c}]_x[N(W)R^1]_y[N(Y)_bR^2{}_{2-b}]_z(HX)_w \quad (I)$$

wherein R and R¹ are individually selected from the group consisting of divalent alkylene groups containing from two to six carbon atoms inclusive, divalent arylene groups containing from six to twelve carbon atoms inclusive, divalent alkyl substituted arylene groups containing from seven to twenty carbon atoms inclusive, and a divalent group of the formula

—CR³— wherein R³ is a divalent alkylene group containing from two to six carbon atoms inclusive; R² is a monovalent alkyl or aryl group containing from one to ten carbon atoms or hydrogen; W is either hydrogen, or

—CR⁴ wherein R⁴ is a monovalent hydrocarbon group containing from 8 to 24 carbon atoms and containing at least one double bond; Y is selected from the group consisting of hydrogen;

—CR⁴ wherein R⁴ is as defined above; R²; and —R⁵Si(OR⁶)₃₋ₐ(R⁷)ₐ wherein R⁵ is a divalent alkylene group containing from two to six carbon atoms inclusive, R⁶ and R⁷ are individually a monovalent alkyl or aryl group containing from one to six carbon atoms inclusive; and R⁶ may also be a silicon containing moiety wherein the oxygen atom is directed bonded to the silicon atom of the R⁶ silicon containing moiety; and a has a value of zero, one, or two; b has a value of zero, one or two; c has a value of zero or one; x and y have values such that x+y equal one to thirty with the proviso that x is at least one; z is zero or one; X is as hereinafter defined; w has a value equal to from zero to the sum of x+y+z provided that w does not exceed the total nitrogen atom in free amine form; with the proviso that at least one Y is —R⁵Si(OR⁶)₃₋ₐ(R⁷)ₐ; and at least one other Y is

—CR⁴.

DETAILED DESCRIPTION OF THE INVENTION

The class of fatty ethenoid acylaminoorganosilicon compounds represented by formula I above can be prepared by a variety of known techniques. The basic reaction is the acylation of an aminoorganosilane by reaction with a carboxylic organic acid, a carboxylic organic acid halide, an ester or anhydride derivative of a carboxylic organic acid. The aminoorganosilanes suitable for acylation in the instant invention are represented by the formula:

$$Y[N(Y)_cR_{2-c}]_x[N(W)R^2]_y[N(Y)_bR^2{}_{2-b}]_z$$

wherein Y is as defined above but excluding

—CR⁴ and X, R, R¹, R², b, c, x, y and z are as defined above. At least one Y must be —R⁵Si(OR⁶)₃₋ₐ(R⁷)ₐ and at least one other Y must be hydrogen.

Preferably, the aminoorganosilanes are such that R and R¹ are ethylene or propylene, R² is methyl or hydrogen, R⁵ is propylene, R⁶ and R⁷ are methyl or ethyl, a=0 or 1, b=0 or 1, c=1, x=1 to 4, y=0 to 3 and z=0 or 1. Illustrative of such primary and secondary aminoorganosilanes are bis-(3-trimethoxysilylpropyl)a- mine, gamma-aminopropyltriethoxysilane, gamma-aminopropylmethyldiethoxysilane, gamma-aminopropylethyldiethoxysilane, gamma-aminopropylethyldimethoxysilane, gamma-aminopropylphenyldiethoxysilane, delta-aminobutyltriethoxysilane, delta-aminobutylmethyldiethoxysilane, delta-aminobutylethyldiethoxysilane, delta-aminobutylphenyldiethoxysilane, 2-amino-1-methylethyltriethoxysilane, N-methyl-gamma-aminopropyltriethoxsilane, N-phenyl-gamma-aminopropyltriethoxsilane, N-butyl-gamma-aminopropylmethyldiethoxysilane and the like.

Suitable acylation reagents are those represented by the general formula $$R^4-\overset{\overset{\displaystyle O}{\|}}{C}-X$$

where $R^4$ is a monovalent hydrocarbon group containing anywhere from 8 to 24 carbon atoms and at least one double bond and X is a halogen atom, a hydroxyl group, an ester group ($-OR^8$) or an anhydride group ($-OCOR^9$). Wherein $R^8$ and $R^9$ are individually monovalent hydrocarbon groups. Although such a composition may be synthetically prepared from petroleum based materials and as such used in the present invention, it is preferred to employ those materials derived from a fatty acid (hence the term "fatty" will be employed herein; however it should not be construed to mean the acids are derived solely from non-petroleum based materials). Fatty acids are principally derived from the body fat of animals, such as lard and tallow; from fruit pulp, such as palm and olive; the seed of plants, such as cottonseed, peanut, corn, safflower, sesame, sunflower, rapeseed, mustardseed, soybean, and linseed; and the like.

Common monoethenoid fatty acids include abtusilic, capraleic, 10-undecylenic, lauroleic, physeteric, myristoleic, palmitoleic, petroselinic, petroselaidic, oleic, elaidic, vaccenic, gadoleic, cetaleic, erucic, brassidic, selacholeic, ximenic and lumequoic to name but a few.

The polyethenoid fatty acids include, but are not limited to sorbic, linoleic, linolelaidic, hiragonic, eleostearic, punicic, linolenic, ricinoleic, elaidolinolenic, psuedoelectrostearic, moroctic, parinaric, arachidonic, clupanodonic, nisinic and the like.

The fatty acids useful in the present invention are considered to include both those containing conjugated as well as nonconjugated double bonds.

Preferably, the fatty acid contains eight to eighteen carbon atoms; more preferably the fatty acid is one derived from linseed. Such fatty acids are commercially available, such as from Procter & Gamble, and contain an assortment of fractions. Illustrative of the fractional content of a commercial grade linseed acid are the data in Table I below.

TABLE I

| FRACTION | PERCENT (WEIGHT) |
|---|---|
| $C_{14}$, $C_{12}$, $C_{10}$, $C_8$, and lowers | 1.6 ± 0.1% |
| $C_{16}$ palmitic | 5.5 ± 0.3% |
| $C_{18}$ stearic | 3.6 ± 0.2% |
| $C_{18}$ oleic 1 × (=) | 17.9 ± 0.9% |
| $C_{18}$ linoleic 2 × (=) | 18.0 ± 0.9% |
| $C_{18}$ linolenic 3 × (=) | 50.7 ± 2.5% |
| higher than $C_{18}$ | 2.7 ± 0.2% |

The free fatty acid is converted to the acylation reagents by well known techniques. For instance, when X is to be halogen, the fatty acid is converted at room temperature or higher by simple addition of thionyl halide to the fatty acid and thereafter removal of sulfur dioxide and hydrogen chloride is effected. If a fatty acid ester is desired, it is obtained by catalyzed esterification with alcohols and fatty acid and removal of by-product water. If the anhydride derivative is desired the anhydride derivative is produced by catalyzed dehydration of the fatty acid. Most, if not all, of these acylation reagents are commercially available.

The details as to the acylation reaction conditions between the monoprimary and/or secondary aminosilane and the carboxylic organic acid or derivative are more fully set forth in U.S. Pat. No. 2,929,829 issued Mar. 22, 1960.

Where monoaminoorganosilicon compounds are reacted with carboxylic organic acid halides, a tertiary alkyl amine, such as $Et_3N$ or pyridine may be employed to remove the HX and aid the completion of the acylaminoorganosilicon compound. In other instances an excess of aminoorganosilicon compound instead of the tertiary alkyl amine or pyridine is used to produce a mixture of aminoorganosilicon hydrogen halide and the corresponding fatty ethenoid acylaminoorganosilicon compound. In this latter approach the aminoorganosilicon hydrogen halide compounds remain as a water compatible co-reactive silane component which in some instances may provide a substantial benefit to end use handling and performance of the coating for glass articles.

An illustrative reaction between acylation reagents and aminoorganosilanes with primary and secondary amino groups is depicted below:

$$C_{17}H_{29}\overset{\overset{\displaystyle O}{\|}}{C}Cl + NH_2CH_2CH_2NH(CH_2)_3Si(OCH_3)_3 \longrightarrow$$

$$C_{17}H_{29}\overset{\overset{\displaystyle O}{\|}}{C}NHCH_2CH_2NH(CH_2)_3Si(OCH_3)_3 \cdot HCl$$

For many coating applications it is preferred to use carboxylic acid chloride acylating reagents because they are readily available, highly reactive and least complicated by undesirable side reactions. Optional removal of HCl is sometimes advantageous.

Aminoorganosilanes having two or more amino groups and one or more silane groups are reacted with carboxylic organic acid halide to obtain a fatty ethenoid acylaminoorganosilicon compound which can have a combination of fatty acylamino, free amino and amine hydrogen halide groups as well as one or more silane groups.

Suitable aminoorganosilanes containing two or more amino groups include, but are not limited to, N-beta-(aminoethyl)-gamma-aminopropyltrimethoxysilane; N-beta-(aminoethyl)-N-beta-(aminoethyl)-gamma-aminopropyltrimethoxysilane; $(CH_3CH_2O)_3SiCH_2CH_2CH_2NHCH_2CH_2NH_2$, $(C_2H_5O)_2(CH_3)SiCH_2CH_2CH_2(NHCH_2CH_2)_3NHCH_2CH_2CH_2Si(CH_3)(OC_2H_5)_2$, $(CH_3O)_3SiCH_2CH_2CH_2NHCH_2C_6H_4NH_2$ $(CH_3O)_2(CH_3)SiCH_2CH_2CH_2NHCH_2CH_2NHCH_2CH_2CH_2Si(CH_3)(OCH_3)_2$ $(CH_3O)_3SiCH_2CH_2CH_2NHCH_2CH_2NHCH_2CH_2CH_2Si(OCH_3)_3$ Once again, reference is made to U.S. Pat. No. 2,929,829 for particulars relative to reaction conditions.

For production of water dilutable coatings from polyaminoorgano(poly)silanes, it is preferred to add carboxylic acid chloride slowly to a well stirred solution of silane in methanol, ethanol or the like at from 0° to 150° C. preferably 25°-70° C. The in situ formation of aminoorgano hydrogen halide salt groups which occurs during this reaction provides the product with water solubility or dispersibility. This preferred process for fatty ethanoid acylated derivatives of polyaminoorgano(poly)silane compounds generally is used to produce the same molar concentration of acylated amine and amine hydrogen halide salt groups. The molar concentration of free amino groups will largely depend on the extent of acylation initially undertaken in this process and can vary widely.

The novel compounds of this invention are complex structures, but can be produced by alternate methods.

Preferably, the fatty ethenoid acyl aminoorganosilicon compounds are such that R and $R^1$ are independently alkylene radicals and more preferably ethylene or propylene, $R^2$ is methyl or hydrogen, $R^4$ is a monovalent hydrocarbon radical containing 8 to 24 carbon atoms and at least one double bond, $R^5$ is propylene, $R^6$ and $R^7$ are independently methyl or ethyl, a=0 or 1, b=0 or 1, c=1, x=1 to 4, y=0 to 3 and z=0 or 1, and at least one Y is $-R^5Si(OR^6)_{3-a}(R^7)_a$ and at least one other Y is

Exemplary of the fatty ethenoid acylaminoorganosilicon compounds are set forth in Table II below:

TABLE II (C₂H₅O)₃SiCH₂CH₂[N(CH₂CH₂CH₂Si(OC₂H₅)₃)(C(O)C₁₇H₂₉)]
(C₂H₅O)₃SiCH₂CH₂CH₂[N(H)CH₂CH₂][N(H)C(O)C₁₇H₂₉].[HCl]
(CH₃O)₂(CH₃)SiCH₂CH₂CH₂[N(CH₂CH₂CH₂Si(OCH₃)₂(CH₃))CH₂CH₂][N(C(0)C₁₇H₃₁)CH₂CH₂]₂
[N(H)(CH₂CH₂CH₂Si(OCH₃)₂(CH₃))].[HCl]₂
(CH₃O)₃SiCH₂CH₂CH₂[N(H)CH₂CH₂][N(C(O)(C₁₇H₃₃)CH₂CH₂][N(H)CH₂CH₂CH₂Si(OCH₃)₃].[HCl]
(CH₃O)₃SiCH₂CH(CH₃)[N(H)CH₂C₆H₄CH₂][N(C(O)C₁₇H₃₁)CH₂C₆H₄CH₂][N(H)—CH(CH₃)CH₂Si(OCH₃)₃].[HCl₂]
(CH₃O)₂(CH₃)SiCH₂CH₂CH₂CH₂[N(C(O)C₁₇H₂₉)CH₂CH₂][N(C(O)C₁₇H₂₉)CH₂CH₂CH₂CH₂Si(CH₃)(OCH₃)₂
(C₂H₅O)₃SiCH₂CH₂CH₂N(H)C(O)C₁₇H₂₉
(CH₃O)₃SiCH₂CH₂CH₂N(H)CH₂CH₂N(H)C(O)C₁₇H₂₉.(HCl)
(CH₃O)₃SiCH₂CH₂CH₂N(C(O)C₁₇H₂₉)CH₂CH₂N(H)C(O)C₁₇H₂₉
(CH₃O)₃SiCH₂CH₂CH₂N(C(O)C₁₇H₂₉)CH₂CH₂N(H)CH₂CH₂NH₂.(HCl)
(CH₃O)₃SiCH₂CH₂CH₂N(H)CH₂CH₂N(C(O)C₁₇H₂₉)CH₂CH₂CH₂Si(OCH₃).(HCl)
(CH₃O)₃SiCH₂CH₂CH₂N(C(O)C₁₇H₂₉)CH₂CH₂N(C(O)C₁₇H₂₉)CH₂CH₂CH₂Si(OCH₃)₃
(CH₃O)₃SiCH₂CH₂CH₂[N(H)CH₂CH₂][N(C(O)C₁₇H₂₉)CH₂CH₂CH₂Si(OCH₃)₃].[HCl]
(CH₃O)₃SiCH₂CH₂CH₂[N(CH₂CH₂CH₂Si(OCH₃)₃)(C(O)C₁₇H₂₉)]

In one such method a polyalkyleneamine is reacted with the carboxylic organic acid, its acid halide or anhydride to provide a partial acylamino derivative, which is also an amino containing intermediate that is subsequently silylated by conventional means to provide the acylaminoorganosilicon compound desired.

This latter silylation reaction between partially acylated polyalkyleneamine and organo functional silane is preferably an amine alkylation reaction with a chloroorganosilane ester and generally requires higher reaction temperatures. Usually, it is necessary to premix reactants and heat to between 60° C. and 140° C. Preferably a reaction temperature between 80° and 120° C. is desirable. The reaction can be effected over any reasonable time period to produce some reaction product. It is desirable to follow the course of the reaction by titration of chloride ion. A nonaqueous potentiometric titration of generated chloride ion with standardized silver nitrate serves nicely.

This process has a tendency to produce higher viscosity products with varying amounts of polysiloxane product in place of the full amount of silane ester groups. Subsequent dilute aqueous dispersions also show a somewhat greater tendancy to destabilize with time.

In general, we prefer to silylate polyalkyleneamines according to the teachings of U.S. Pat. No. 3,746,738 and to subsequently acylate as previously described.

In all of the reactions set forth above the desired end product is a fatty ethenoid acylaminoorganosilicon compound selected from the class represented by the general formula:

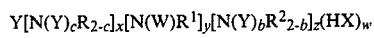

The class of fatty ethenoid acylaminoorganosilicon compounds can be used alone or in combination with a dispersing agent, such as, an organic solvent and/or water. The organic solvent can be any of those commonly used to dissolve or disperse organic coatings, including alcohols, ketones, esters, ethers and the like. These solvents are useful as a vehicle for applying the class of fatty ethenoid acylaminoorganosilicon compounds to the glass surface. When used in combination with a dispersing agent, a preferred composition comprises from 0.01 to 20 weight percent of the fatty ethenoid acylaminoorganosilicon compounds dissolved or dispersed into water. As prepared, it may be applied as hereinafter described.

Another aspect of the instant invention is a three component coating composition wherein the class of fatty ethenoid acylaminoorganosilicon compounds is used in combination with a dispersing agent and an organic polymer and/or fatty acid.

The organic polymer that can be used in combination with the fatty ethenoid acylaminoorganosilicon compounds can be a polyolefin including polyethylene, polypropylene; polyisobutylene; a polyether including polyethylene oxide, polypropylene oxide, and polyethylene oxide polypropylene oxide copolymer; and an epoxy or other polymer that imparts a waxy nature to the coating. A preferred composition comprises forming an aqueous emulsion of the polyolefin. Details for preparing this preferred emulsion are set forth in U.S. Pat. No. 2,995,533, which disclosure is incorporated herein by reference.

The fatty acids that can be used in combination with the fatty ethenoid acylaminoorganosilicon compounds are principally derived from the body fat of animals, such as lard and tallow; from fruit pulp, such as palm and olive; the seed of plants, such as cottonseed, peanut, corn, safflower, sesame, sunflower, rapeseed, mustard-seed, soybean and linseed; and the like.

It should not be construed to mean the acids are derived solely from non-petroleum materials.

Preferably, the fatty acid contains eight to eighteen carbon atoms; more preferably the fatty acids are stearic acid, oleic acid and/or linolenic acid.

The coating for glass articles is prepared by dissolving from 0.01 to 20 weight percent silane from the class of fatty ethenoid acylaminoorganosilicon compounds into water and then dissolving, dispersing or emulsifying from 0.01 to 50 weight percent organic polymer and/or fatty acid.

Preferably, the coating for glass articles is prepared by dissolving from 0.05 to 3 weight percent silane from the class of fatty ethenoid acylaminoorganosilicon compounds into water and then adding 0.05 to 5 weight percent polyolefin in the form of an aqueous emulsion, as described in U.S. Pat. No. 2,995,533.

Another aspect of the instant invention is a two step coating process for glass articles in which 0.01 to 20 weight percent solution of silane from class of fatty ethenoid acylaminoorganosilicon compounds is deposited into the glass surface in one application step followed by depositing an organic polymer and/or fatty acid in a subsequent application step.

In the first application step, the class of fatty ethenoid acylaminoorganosilicon compounds are deposited from an aqueous or organic solution. The organic solvents can be any of those commonly used to dissolve or disperse organic coatings, including alcohols, ketones, esters, ethers, and so on. These solvents are useful as a vehicle for applying the class of fatty ethenoid acylaminoorganosilicon compounds to the glass surface. A preferred composition comprises from 0.05 to 3 weight percent of the fatty ethenoid acylaminoorganosilicon compound dissolved into water.

In the second application step, the organic polymer that is dispersed in an organic solvent and/or water can be a polyolefin including polyethylene; polypropylene; polyisobutylene; a polyether including polyethylene oxide, polypropylene oxide, polyethylene oxide polypropyleneoxide copolymer; and an epoxy or other polymer that imparts a waxy nature to the coating.

Preferably, the organic polymer is applied as an aqueous emulsion of from 0.05 to 5 weight percent polyethylene, as described in U.S. Pat. No. 2,995,533.

The fatty acids that can be deposited on the glass surface in the second application step are the some as those which have been previously described.

The coatings for glass articles described in the instant invention can be applied by any techniques commonly known in the art of coatings including spraying, dipping, wiping, brushing and misting.

A preferable method for applying the coating is to spray a solution of the coatings described in the instant invention into a glass surface that is at a temperature between 90° C. and 250° C.

Although not wishing to be bound by any specific limits on the amount of coating necessary to enhance the surface properties of the glass articles, it is advisable to employ at least 0.1 milligrams of the coating per $cm^2$ of the surface area of the glass article, with approximately 1.5 milligram coating/$cm^2$ being preferred. It should be noted that at the lower coating levels, higher concentrations of the fatty ethenoid acylaminoorganosilicon compound is recommended if a two or three component coating system is employed.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified. For the purposes of these examples Me denotes a methyl group.

EXAMPLES

Example 1

"Fatty" Ethenoid Acylaminoorgano Bis-silane

Into a 1 liter, 3-necked flask equipped with dropping funnel, thermometer, thermosensor, mechanical stirrer, heating mantle, 1 foot ¾" O.D. Vigreaux column, distillation head and receiver was charged 85.3 gms., 0.25 moles of $[(MeO)_3SiCH_2CH_2CH_2]_2NH$, 35.4 gms., 0.35 moles of triethylamine and 194.2 gms. of toluene. Starting at room temperature, through the dropping funnel was added to the stirred mixture 74.2 gms., 0.25 moles of linseed acid chloride. An exotherm resulted throughout the addition and the reaction mixture temperature was held between 30° and 50° C. by external application of a water/ice bath. After an additional hour of stirring at ~35° C. the total reaction mixture was pressure filtered through a 1 micron filter pad and the resulting $Et_3N.HCl$ salt cake was washed with three 50 ml portions of toluene. The combined filtrate and toluene extract of the salt cake were vacuum stripped to 100° C./1 mm Hg pressure to remove toluene, excess triethylamine and any other low boiling components. $^{13}C$, and $^{29}Si$ NMR indicate the product structure is

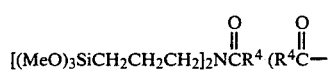

Example 2

"Fatty" Ethenoid Acylaminoorgano Bis-Silane/Aminoorgano Bis-Silane Hydrochloride [50 Mole % Mixture]

In much the same equipment setup as described in Example 1, 85.3 gms., 0.25 moles of $[(MeO)_3Si(CH_2)_3]_2NH$ was stirred at 50° C. while 37.11 gms., 0.125 moles of linseed acid chloride was slowly added through a dropping funnel. An exotherm resulted throughout the addition and external cooling was used to control the reaction temperature between 50° and 60° C. The reaction mixture analyzed for 0.98 meq/gm chloride ion [96% of theoretical]. $^{13}C$ and $^{29}Si$, NMR indicate an equimolar mixture of

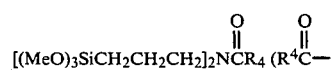

a linseed acid chloride derivative) and $[(MeO)_3SiCH_2CH_2CH_2]_2NH.HCl$.

Example 3

"Fatty" Ethenoid Acylamino 25 Mole % Derivative of Diaminoorgano Bis-Silane

In the same equipment setup described in Example 1, 76.8 gms., 0.2 moles of [(MeO)$_3$SiCH$_2$CH$_2$CH$_2$NHCH$_2$]$_2$ dissolved in 106.7 gms., 3.33 moles of methanol was charged. The homogeneous mixture was stirred at room temperature and 29.7 gms., 0.10 moles of linseed acid chloride was slowly added. An exotherm resulted throughout the addition and air cooling was used to control the reaction temperature between 50° and 60° C. The reaction mixture was heated to reflux methanol for one hour, cooled and analyzed for chloride ion [98.3% of theoretical]. The product mixture at 50 wt.% active in methanol, had a calculated average composition:

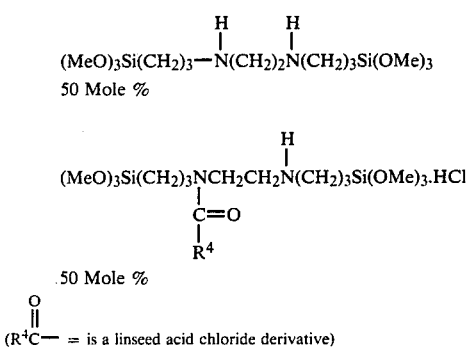

Example 4

"Fatty" Ethenoid Acylaminoorganoamino Bis-Silane Hydrochloride

In much the same manner as described in Example 3, 76.8 gms., 0.2 moles of [(MeO)$_3$SiCH$_2$CH$_2$CH$_2$NHCH$_2$]$_2$ dissolved in 136.4 gms., 4.26 moles of methanol was reacted with 59.4 gms., 0.20 moles of linseed acid chloride. The resulting product, at 50 wt. % active in methanol, has a calculated average composition:

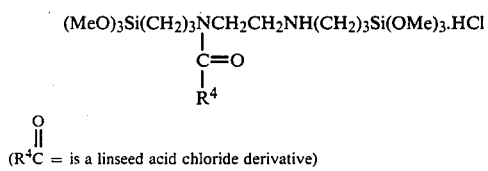

Example 5

Di("Fatty" Ethenoid Acylamino)organo-Bis-Silane

In much the same manner as described in Example 1, 76.8 gms., 0.2 moles of [(MeO)$_3$SiCH$_2$CH$_2$CH$_2$NHCH$_2$]$_2$, 50.6 gms., 0.5 moles of triethylamine and 250 gms. of toluene was reacted with 118.7 gms., 0.4 moles of linseed acid chloride to give the corresponding di("fatty" ethenoid acylamino)organo-bis-silane

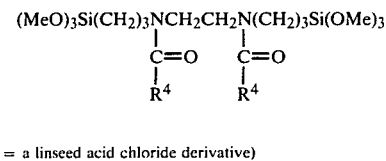

($R^4\overset{O}{\underset{\|}{C}}$ = a linseed acid chloride derivative)

Example 6

"Fatty" Ethenoid Acylamino Hydrochloride Derivative of Triaminoorganosilane

In much the same manner described for Example 3, 265.4 gms., 1.0 mole of NH$_2$CH$_2$CH$_{NHCH2}$CH$_2$NH(CH$_2$)$_3$Si(OMe)$_3$ dissolved in 562.4 gms. of methanol was reacted with 297 gms., 1.0 moles of linseed acid chloride to produce the corresponding "fatty" ethenoid acylamino hydrochloride derivative with the average composition:

$$R^4\overset{O}{\underset{\|}{C}}NHCH_2CH_2NHCH_2CH_2NH(CH_2)_3Si(OMe)_3 \cdot HCl$$

where $R^4$ is a linseed acid chloride derivative

Example 7

"Fatty" Ethenoid Acylamino Hydrochloride Derivative of Diaminoorganosilane

In much the same manner described in Example 3, 222.1 gms. 1.0 moles of NH$_2$CH$_2$CH$_2$NH(CH$_2$)$_3$Si(OMe)$_3$, dissolved in 519.1 gms. of methanol, was reacted with 297 gms., 1.0 moles of linseed acid chloride to produce the corresponding "fatty" ethenoid acylamino hydrochloride derivative with the average composition:

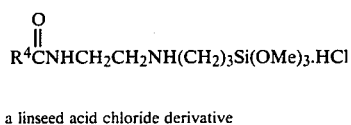

Example 8

Evaluation of Fatty Ethenoid Acylaminoorganosilicon Compound as a Coating for Glass Articles The procedure used to evaluate the performance of the experimental coatings was as follows:
1. Preparation of the Coating for Glass Articles that is comprised of fatty ethenoid acylaminoorganosilicon compounds and organic polymer.

To 98.1 parts water are added 0.4 parts of the "fatty" ethenoid acylamino organosilicon compound that is illustrated by the formula; C$_{17}$H$_{29}$CONHCH$_2$CH$_2$NHCH$_2$CH$_2$NHCH$_2$-$_2$Si(OCH$_3$)$_3$·HCl which is dissolved in methanol (50 weight percent). After the pH is adjusted to 11.52, 1.5 parts of aqueous emulsion of polyethylene that is 20% solids by weight is added with stirring at room temperature. The preparation of the polyethylene emulsion is disclosed in U.S. Pat. No. 2,995,533.
2. Bottle Coating Procedure Test bottles are washed with acetone and heated in an oven to 565° C. for at least 4 hours to clean the glass surface, and then cooled to 177° C. The bottles are then removed from the oven and immediately suspended from the shaft of an electric motor that is rotating at 50 rpm and are sprayed with the aqueous emulsion of the "fatty" ethenoid acylaminoorganosilicon compound and the polyethylene for 3 revolutions. A Devilbiss spray gun, Model #EGA-502, set for a fan pattern and siphon feed using 20 psi air pressure is used. The distance between the spray gun nozzle and the glass bottle is 18 inches. This spraying technique deposits approximately 0.037 g/cm² of the aqueous emulsion onto the glass surface. The coating quickly dries to form a clear, colorless film. The bottle is then removed and allowed to cool to room temperature before the bottles are tested.

3. Testing Procedures

Scratch Test

Scratch resistance is measured on a laboratory scale static load tester. The device slides the surfaces of two bottles together at 45 degree angle under constant load. Load settings can be varied from 10 to 100 pounds. The bottles pass at a particular load setting if no nicks are seen in the area of the test. Bottles are tested both wet and dry. In the wet test, the bottles are sprayed with a fine mist of water just prior to the test.

Lubricity Test

Lubricity is expressed in terms of slip angle. Slip angle is measured on a motorized tilting table (manufactured by the American Glass Research Corporation). Three coated bottles are arranged in a pyramid on their sides on the table. The two bottom bottles are held in place and the third allowed to move. The table is tilted at a slow constant rate until the top bottle slips approximately one-quarter inch (¼"). The angle at the point of slippage between the plane of the bottom of the two bottles and the horizontal is measured and recorded as the slip angle.

Label Adhesion

The test method for determining label adhesion is performed in accordance with ASTM method D-3359-58. The labels are first coated with an adhesive (2 to 3 mils) at room temperature. The application is done by means of a wet film knife (5 mils wet). The bottles, affixed with labels, are heated at 60° C. for twenty minutes. After cooling to room temperature, a crosscut of ~¾" is made at an angle of 90° on the label. The grid area is examined to determine the extent of label adhesion as follows:

0 (less than 50% of label remains on bottom after crosscut)
1 (~50% of label remains on bottle after crosscut)
2 (75% of label remains on bottle after crosscut)
3 (90% of label remains on bottle after crosscut) 4 (95% of label remains on bottle after crosscut)
5 (100% of label remains on bottle after crosscut)

A total of three crosscuts are made at random areas on the label with the average classification reported.

Aqueous Caustic Wash

The aqueous caustic wash consists of submerging a bottle into 70° C., 5% by weight sodium hydroxide solution for 30 minutes, and then thoroughly rinsed with distilled water.

Appearance

A qualitative judgment of the coating's appearance is made by shining a bright light on the bottle in a dark room.

Results

The test results for the aqueous mixture of 0.2 weight percent

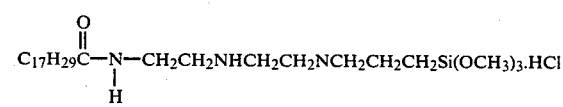

and 0.3 weight percent solid polyethylene are given in Table III, Compound 1. Also shown in Table III are the commercial coatings and representative mixtures of 0.2 wt. percent acylaminosilanes, which *do not* belong to the "fatty" ethenoid acylaminosilicon compounds and 0.3 weight percent polyethylene. As is clearly evident, the wet scratch and dry scratch after caustic wash are superior for the "fatty" ethenoid acylaminoorganosilicon based coating.

TABLE III

| Coating[1] | Appearance | TEST DATA BEFORE CAUSTIC WASH | | | | | | TEST DATA AFTER CAUSTIC WASH | |
|---|---|---|---|---|---|---|---|---|---|
| | | Lubricity (dry/wet) | Scratch (dry/wet) lbs | Casein | Vinyl dex ™ | Polyvinyl Acetate | Jelly Gum | Lubricant (dry/wet) | Scratch (dry/wet) lbs |
| 8 | good | 12°/10° | 100/90 | 0 | 0 | 1 | 0 | 12°/9° | 90/— |
| A | excellent | 11°/10° | 100/100 | 0 | 0 | 3 | 0 | 13°/7° | 100/100 |
| B | good | 11°/13° | 90/10 | 1 | 0 | 2 | 0 | 25°/26° | 50/10 |
| C | good | 12°/23° | 50/10 | 0 | 0 | 2 | 0 | 13°/36° | 20/— |
| D | good | 13°/21° | 50/30 | 0 | 0 | 1 | 0 | 12°/26° | 80/— |
| E | good | 12°/15° | 60/30 | 2 | 0 | 1 | 0 | 11°/17° | 30/— |
| F | good | 11°/18° | 70/20 | 0 | 0 | 1 | 0 | 13°/42° | 20/— |
| G | good | 12°/16° | 60/20 | 1 | 0 | 2 | 0 | 13°/41° | 20/— |

TABLE III-continued

| | | | | | | | | | |
|---|---|---|---|---|---|---|---|---|---|
| H | good | 12°/24° | 70/20 | 1 | 0 | 3 | 0 | 14°/40° | 20/— |

[1]The composition of the glass coating dissolved in water at pH 11.5

8. 0.2 wt % $C_{17}H_{29}\overset{O}{\overset{\|}{C}}$—NHCH$_2$CH$_2$NHCH$_2$CH$_2$NHCH$_2$CH$_2$CH$_2$Si(OCH$_3$)$_3$.HCl + 0.3 wt % polyethylene A. Two step coating: 1. SnCl$_2$ Sprayed. 2. 0.2 wt % polyethylene sprayed.

B. 0.2 wt % CH$_3\overset{O}{\overset{\|}{C}}$NHCH$_2$CH$_2$NHCH$_2$CH$_2$NHCH$_2$CH$_2$CH$_2$Si(OCH$_3$)$_3$.HCl + 0.3 wt % polyethylene.

C. 0.2 wt % CH$_2$=CH$_2\overset{O}{\overset{\|}{C}}$NHCH$_2$CH$_2$NHCH$_2$CH$_2$NHCH$_2$CH$_2$CH$_2$Si(OCH$_3$)$_3$.HCl + 0.3 wt % polyethylene.

D. 0.2 wt % CH$_3$CH$_2$CH$_2\overset{O}{\overset{\|}{C}}$NHCH$_2$CH$_2$NHCH$_2$CH$_2$NHCH$_2$CH$_2$CH$_2$Si(OCH$_3$).HCl + 0.3 wt % polyethylene.

E. 0.2 wt % CH$_3$(CH$_2$)$_4\overset{O}{\overset{\|}{C}}$HN(CH$_2$CH$_2$NH)$_2$CH$_2$CH$_2$CH$_2$Si(OCH$_3$)$_3$.HCl + 0.3 wt % polyethylene.

F. 0.2 wt % CH$_3$CH=CH$\overset{O}{\overset{\|}{C}}$NH(CH$_2$CH$_2$NH)$_2$CH$_2$CH$_2$CH$_2$Si(OCH$_3$)$_3$.HCl + 0.3 wt % polyethylene.

G. 0.2 wt % CH$_2$=C(CH$_3$)$\overset{O}{\overset{\|}{C}}$NH(CH$_2$CH$_2$NH)$_2$CH$_2$CH$_2$CH$_2$Si(OCH$_3$)$_3$.HCl = 0.3 wt % polyethylene.

H. 0.2 wt % HO$\overset{O}{\overset{\|}{C}}$CH=CH$\overset{O}{\overset{\|}{C}}$NH(CH$_2$CH$_2$NH)$_2$CH$_2$CH$_2$CH$_2$Si(OCH$_3$)$_3$.HCl + 0.3 wt % polyethylene.

Examples 9–17

The coatings Nos. 9–17 are made, applied and tested as described in Example 8. Although the dry scratch resistance after caustic wash for coating No. 9–17, (Table IV) are less than for Coating No. 1, (Table III), the adhesion of common adhesives (casein, Vinyl Dex ™, polyvinyl acetate and jelly gum) is considerably better, especially for coating No. 13 and 16, (Table IV).

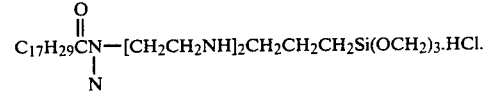

After the pH is adjusted to 11.5, 1.5 parts of an aqueous emulsion of polyethylene that is 20% solids by weight is added with stirring at room temperature. The preparation of the polyethylene emulsion is disclosed in U.S.

TABLE IV

| Coating[1] | Appearance | TEST DATA BEFORE CAUSTIC WASH | | | | | | TEST DATA AFTER CAUSTIC WASH | |
|---|---|---|---|---|---|---|---|---|---|
| | | Lubricity (dry/wet) | Scratch (dry/wet) lbs | Casein | Vinyl dex ™ | Polyvinyl Acetate | Jelly Gum | Lubricant (dry/wet) | Scratch (dry/wet) lbs |
| 9 | good | 11°/18° | 70/— | 2 | 1 | — | — | 11°/13° | 40/— |
| 10 | good | 10°/12° | 70/60 | 2 | 0 | 2 | 0 | 19°/38° | 30/— |
| 11 | good | 11°/12° | 50/50 | 3 | 0 | 1 | 0 | 11°/17° | 10/— |
| 12 | good | 12°/10° | 70/50 | 2 | 0 | 1 | 0 | 12°/11° | 30/— |
| 13 | good | 11°/13° | 90/50 | 3 | 0 | 3 | 0 | 11°/11° | 40/— |
| 14 | good | 11°/16° | 70/50 | 2 | 0 | 4 | 1 | 10°/14° | 50/— |
| 15 | good | 12°/13° | 50/40 | 2 | 0 | 2 | 0 | 11°/12° | 20/— |
| 16 | good | 11°/15° | 100/60 | 2 | 0 | 4 | 1 | 10°/12° | 40/— |
| 17 | good | 11°/17° | 70/60 | 3 | 0 | 1 | 0 | 10°/12° | 40/— |

[1]Coating Nos. 9–17 are Composed of an Aqueous Emulsion of 0.3 wt % Polyethylene and 0.2 wt % "Fatty" Ethenoid Acylaminoorganosilicon Compounds with the Structures 9–17.

| Compound in Coating No. | Polyamine | Functional groups (moles/mole of polyamine) | | | |
|---|---|---|---|---|---|
| | | $[R^4\overset{O}{\overset{\|}{C}}-]$ | $[C_3H_6Si(OCH_3)_3]$ | [HCl] | [H] |
| 9 | NH$_2$CH$_2$CH$_2$NH$_2$ | 1 | 1 | 1 | 0 |
| 10 | NH$_2$CH$_2$CH$_2$NHCH$_2$CH$_2$NH$_2$ | 1.4 | 1.2 | 1.2 | 0.4 |
| 11 | NH$_2$CH$_2$CH$_2$NHCH$_2$CH$_2$NH$_2$ | 1.2 | 1.6 | 1.6 | 0.2 |
| 12 | NH$_2$(CH$_2$CH$_2$NH)$_2$CH$_2$CH$_2$NH$_2$ | 2.0 | 1.0 | 1.0 | 1.0 |
| 13 | NH$_2$(CH$_2$CH$_2$NH)$_2$CH$_2$CH$_2$NH$_2$ | 2.0 | 1.4 | 1.4 | 0.6 |
| 14 | NH$_2$(CH$_2$CH$_2$NH)$_2$CH$_2$CH$_2$NH$_2$ | 2.0 | 1.7 | 1.7 | 0.3 |
| 15 | NH$_2$(CH$_2$CH$_2$NH)$_3$CH$_2$CH$_2$NH$_2$ | 2.0 | 1.0 | 1.0 | 2.0 |
| 16 | NH$_2$(CH$_2$CH$_2$NH)$_3$CH$_2$CH$_2$NH$_2$ | 2.0 | 1.7 | 1.7 | 1.3 |
| 17 | NH$_2$(CH$_2$CH$_2$NH)$_3$CH$_2$CH$_2$NH$_2$ | 2.0 | 2.5 | 2.5 | 0.5 |

$R^4\overset{O}{\overset{\|}{C}}$— is a linseed acid chloride derivative.

Examples 18–20

To 98 parts water are added varying amounts of

Pat. No. 2,995,533. The coating and testing procedures are described in Example 8. Data are given in Table V.

TABLE V

| Coating No. | Concn of silane (wt. %) | Appearance | Scratch (dry/wet) | Lubricity (dry/wet) | Availability Casein | Availability Vinyl dex TM | Polyvinyl Acetate |
|---|---|---|---|---|---|---|---|
| 18 | 0.1 | good | (80/70) | (10/90) | 0 | 0 | 1 |
| 19 | 0.2 | good | (100/90) | (10/90) | 0 | 0 | 1 |
| 20 | 0.5 | good | (70.70) | (12°/15°) | 0 | 0 | 0 |

Examples 21–26

To 98 parts water is added 0.5 parts

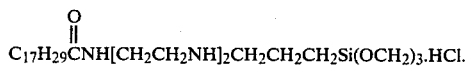

After the pH is adjusted to 11.5, 1.5 parts of an aqueous emulsion of polyethylene that is 20% solids by weight is added with stirring at room temperature. The preparation of the polyethylene emulsion is disclosed in U.S. Pat. No. 2,995,533. The coating and testing procedures are described in Example 8, except that the temperature of the glass surface is varied during the spraying operation Data are given in Table VI.

TABLE VI

| Temperature of glass surface (°F.) | Scratch (dry/lbs) | Lubricity (dry) | Labelability casein | Labelability Vinyldex TM | Polyvinyl Acetate |
|---|---|---|---|---|---|
| 75 | 50 | 16° | 2 | 0 | 3 |
| 100 | 70 | 13° | 1 | 0 | 4 |
| 200 | 70 | 14° | 2 | 0 | 3 |
| 250 | 70 | 14° | 4 | 2 | 3 |
| 300 | 70 | 14° | 2 | 1 | 4 |
| 350 | 70 | 14° | 1 | 0 | 2 |

Examples 27–30

Into 99 parts water is added 1 part fatty ethenoid acylaminoorganosilicon compound and the pH is adjusted to 7 (Solution A).

Into 98.5 parts water is added 1.5 parts aqueous emulsion of 20% solids polyethylene. The preparation of the polyethylene emulsion is disclosed in U.S. Pat. No. 2,995,533 (Solution B).

Bottle Coating Procedure

Test bottles are washed with acetone and heated in an oven to 565° C. for at least 4 hours to clean the glass surface, and then cooled to 177° C. The bottles are then removed from the oven and immediately suspended from the shaft of an electric motor that is rotating at 50 rpm and are sprayed with Solution A for 3 revolutions. A Devilbiss spray gun, Model #EGA-502, set for a fan pattern and siphon feed using 20 psi air pressure is used. The distance between the spray gun nozzle and the glass bottle is 18 inches. Within 1 minute, the glass bottles are sprayed with Solution B under similar conditions as that used for spraying Solution A. The bottle are allowed to cool and then they were tested according to the procedure outlined in Example 8. Data are given in Table VII.

TABLE VII

| Coating[1] | Appearance | Scratch (dry/wet) lbs | Lubricity (dry/wet) | Labelability Casein | Labelability VinylDex TM | Polyvinyl Acetate |
|---|---|---|---|---|---|---|
| 27 | good | (100/40) | (13°/16°) | 1 | 0 | 2 |
| 28 | good | (100/50) | (12°/13°) | 3 | 0 | 0 |
| 29 | good | (100/70) | (13°/16°) | — | 0 | — |
| 30 | good | (80/60) | (10°/15°) | — | 0 | — |

[1]The composition of Solution A.

| Compound in Coating No. | Concn. of silane (wt. %) | Structure |
|---|---|---|
| 27 | 1.0 | $R^4\overset{O}{\underset{\parallel}{C}}N[CH_2CH_2CH_2Si(OCH_3)_3]_2$ |
| 28 | 0.5 | $(CH_3O)_3SiCH_2CH_2CH_2NHCH_2CH_2NHCH_2CH_2CH_2Si(OCH_3)$ |
| | 0.5 | $(CH_3O)_3SiCH_2CH_2CH_2N(C(O)R^4)CH_2CH_2NHCH_2CH_2CH_2Si(OCH_3)_3$ |
| 29 | 1.0 | $R^4\overset{O}{\underset{\parallel}{C}}NHCH_2CH_2NHCH_2CH_2CH_2Si(OCH_3)_3 \cdot HCl$ |
| 30 | 1.0 | $R^4\overset{O}{\underset{\parallel}{C}}NH(CH_2CH_2NH)_2CH_2CH_2CH_2Si(OCH_3)_3 \cdot HCl$ |

($R^4\overset{O}{\underset{\parallel}{C}}-$ is a linseed acid chloride derivative).

Examples 31–38

Into 99 parts water is added 1 part of the fatty ethenoid acylaminoorganosilicon compound. The bottle is coated and tested as described in Example 8.

TABLE VIII

| TEST DATA BEFORE CAUSTIC WASH[2] | | | TEST DATA AFTER CAUSTIC WASH[2] | |
|---|---|---|---|---|
| Lubricity | Scratch | Polyvinyl | Lubricity | Scratch |

TABLE VIII-continued

| Coating[1] | Appearance | (dry/wet) | (dry/wet) lbs | Casein | Vinyl dex TM | Acetate | Appearance | (dry/wet) | (dry/wet) lbs |
|---|---|---|---|---|---|---|---|---|---|
| 31 | good | 12°/11° | 60/60 | 2 | 0 | 2 | good | 18°/14° | 10/— |
| 32 | good | 15°/14° | 40/40 | 4 | 0 | 1 | good | 23°/13° | 20/— |
| 33 | good | 9°/8° | 60/70 | 2 | 0 | 1 | good | 18°/12° | 40/— |
| 34 | good | 12°/11° | 40/60 | 3 | 0 | 2 | good | 19°/11° | 20/— |
| 35 | good | 10°/9° | 40/70 | 2 | 0 | 1 | good | 16°/13° | 10/— |
| 36 | good | 16°/14° | 40/40 | 2 | 0 | 2 | good | 21°/21° | 30/— |
| 37 | good | 14°/13° | 30/40 | 4 | 1 | 2 | good | 23°/18° | 40/— |
| 38 | good | 10°/8° | 50/70 | 4 | 0 | 0 | good | 14°/11° | 10/— |

[1]Coatings Nos. 31-38 are Composed of an Aqueous Solution of 1.0 wt % "Fatty" Ethenoid Acylaminoorganosilicon Compounds with Structures 31-38.

| | | Functional groups (moles/mole of polyamine) | | | |
|---|---|---|---|---|---|
| Compound in Coating No. | Polyamine | $[R^4\overset{O}{\overset{\|}{C}}-]$ | $[C_3H_6Si(OCH_3)_3]$ | [HCl] | [H] |
| 31 | $NH_2CH_2CH_2NHCH_2CH_2NH_2$ | 1.4 | 1.2 | 1.2 | 0.4 |
| 32 | $NH_2CH_2CH_2NHCH_2CH_2NH_2$ | 1.2 | 1.6 | 1.6 | 0.2 |
| 33 | $NH_2(CH_2CH_2NH)_2CH_2CH_2NH_2$ | 2.0 | 1.0 | 1.0 | 1.0 |
| 34 | $NH_2(CH_2CH_2NH)_2CH_2CH_2NH_2$ | 2.0 | 1.4 | 1.4 | 0.6 |
| 35 | $NH_2(CH_2CH_2NH)_2CH_2CH_2NH_2$ | 2.0 | 1.7 | 1.7 | 0.3 |
| 36 | $NH_2(CH_2CH_2NH)_3CH_2CH_2NH_2$ | 2.0 | 1.0 | 1.0 | 2.0 |
| 37 | $NH_2(CH_2CH_2NH)_3CH_2CH_2NH_2$ | 2.0 | 1.7 | 1.7 | 1.3 |
| 38 | $NH_2(CH_2CH_2NH)_3CH_2CH_2NH_2$ | 2.0 | 2.5 | 2.5 | 0.5 |

($R^4\overset{O}{\overset{\|}{C}}-$ is a linseed acid chloride derivative)

[2]The physical properties shown in Table VIII change with time. Lubricity angle increases and scratch resistance (lbs) decreases. The origin of this effect is not known.

I claim:

1. A novel coating composition comprising:
(a) a fatty ethenoid acylaminoorganosilicon compound represented by the formula:

$$Y[N(Y)_cR_{2-c}]_x[N(W)R^1]_y[N(Y)_bR_{2-b}^2]_z(HX)_w \quad (I)$$

wherein R and $R^1$ are individually selected from the group consisting of divalent alkylene groups containing from two to six carbon atoms inclusive, divalent arylene groups containing from six to twelve carbon atoms inclusive, divalent alkyl substituted arylene groups containing from seven to twenty carbon atoms inclusive, and a divalent group of the formula $$-\overset{O}{\overset{\|}{C}}R^3-$$

wherein $R^3$ is a divalent alkylene group containing from two to six carbon atoms inclusive; $R^2$ is a monovalent alkyl or aryl group containing from one to ten carbon atoms or hydrogen; W is either hydrogen, or $$-\overset{O}{\overset{\|}{C}}R^4$$

wherein $R^4$ is a monovalent hydrocarbon group containing from 8 to 24 carbon atoms and containing at least one double bond; Y is selected from the group consisting of hydrogen;

$$-\overset{O}{\overset{\|}{C}}R^4$$

wherein $R^4$ is as defined above; $R^2$; and $-R^5Si(OR^6)_{3-a}(R^7)_a$ wherein $R^5$ is a divalent alkylene group containing from two to six carbon atoms inclusive, $R^6$ and $R^7$ are individually a monovalent alkyl or aryl group containing from one to six carbon atoms inclusive; and $R^6$ may also be a silicon containing moiety wherein the oxygen atom is directly bonded to the silicon atom of the $R^6$ silicon containing moiety; X is selected from the group consisting of a halogen atom, a hydroxy group, an ester group and an anhydride group and a has a value of zero, one, or two; b has a value of zero, one or two; c has a value of zero or one; x and y have values such that $x+y$ equal one to thirty with the proviso that x is at least one; z is zero or one; w has a value equal to from zero to the sum of $x+y+z$ provided that w does not exceed the total nitrogen atom in free amine form; with the proviso that at least one Y is $-R^5Si(OR^6)_{3-a}(R^7)_a$; and at least one other Y is $$-\overset{O}{\overset{\|}{C}}R^4;$$

(b) a dispersing agent; and
(c) an organic polymer.

2. The coating composition of claim 1 wherein the dispersing agent is water or an organic solvent or a combination thereof.

3. The coating composition of claim 1 wherein the organic polymer is selected from the group consisting of polyolefins, polyethers and epoxies.

4. The coating composition of claim 1 wherein the fatty ethenoid acylaminoorganosilicon compound comprises 0.01 to 20 weight percent of the coating composition.

5. The coating composition of claim 2 wherein the dispersing agent comprises from 30 to 99.98 weight percent of the coating composition.

6. The coating composition of claim 3 wherein the organic polymer comprises from 0.01 to 50 weight percent of the coating composition.

7. The coating composition of claim 4 wherein the fatty ethenoid acylaminoorganosilicon compound represents 0.05 to 3 weight percent of the coating composition.

* * * * *